United States Patent
Lee et al.

(10) Patent No.: US 10,697,917 B2
(45) Date of Patent: Jun. 30, 2020

(54) IC AND SENSOR FOR MEASURING SALINITY AND METHOD FOR MEASURING SALINITY USING THE SENSOR

(71) Applicant: 3A LOGICS Co., LTD., Seongnam-si, Gyeonggi-do (KR)

(72) Inventors: Pyeong Han Lee, Seongnam-si (KR); Kwang Beom Park, Seongnam-si (KR); Sung Hun Chun, Gunpo-si (KR); Chang Ho Ryu, Seongnam-si (KR); Sung Wan Kim, Gwangju-si (KR)

(73) Assignee: 3A LOGICS Co., LTD., Seongnam-si (KR)

( * ) Notice: Subject to any disclaimer, the term of this patent is extended or adjusted under 35 U.S.C. 154(b) by 24 days.

(21) Appl. No.: 16/186,638

(22) Filed: Nov. 12, 2018

(65) Prior Publication Data
US 2020/0110049 A1    Apr. 9, 2020

(30) Foreign Application Priority Data

Oct. 4, 2018 (KR) .................. 10-2018-0118018
Oct. 4, 2018 (KR) .................. 10-2018-0118024

(51) Int. Cl.
*G01R 27/00* (2006.01)
*G01N 27/02* (2006.01)
(Continued)

(52) U.S. Cl.
CPC .............. *G01N 27/02* (2013.01); *G01N 33/02* (2013.01); *H04B 5/0043* (2013.01)

(58) Field of Classification Search
CPC ........ G01N 27/02; G01N 27/26; G01N 33/02; G01N 33/492; G01N 33/48792;
(Continued)

(56) References Cited

U.S. PATENT DOCUMENTS 5,735,887 A * 4/1998 Barreras, Sr. ............ A61N 1/08
607/60
8,305,214 B2 * 11/2012 Hyde ....................... H04Q 9/00
340/10.1
(Continued)

FOREIGN PATENT DOCUMENTS

JP    2008175819    7/2008
JP    2018040777    3/2018
(Continued)

*Primary Examiner* — Thang X Le

(57) ABSTRACT

An integrated circuit includes a bi-directional signal transmission pin connected to a sensing electrode of a salinity sensor, an RF interface which generates operating voltages on the basis of an RF signal received through an antenna, different types of driving signal generators having a structure in which each output terminal is connected to the pin, different types of analog-to-digital converters having a structure in which each input terminal is connected to the pin, and a microcontroller unit which generates a first control signal and a second control signal according to a type of the salinity sensor, in which one of the different types of driving signal generators is enabled based on the first control signal, one of the different types of analog-to-digital converters is enabled based on the second control signal, and the operating voltages are supplied to an enabled signal generator and an enabled analog-to-digital converter.

16 Claims, 6 Drawing Sheets

(51) Int. Cl.
*G01N 33/02* (2006.01)
*H04B 5/00* (2006.01)

(58) Field of Classification Search
CPC ...... G01N 33/50; H05B 5/0043; G06K 19/07; G06K 19/077
See application file for complete search history.

(56) References Cited

U.S. PATENT DOCUMENTS

| | | | |
|---|---|---|---|
| 8,542,023 B2* | 9/2013 | Potyrailo | G01N 27/02 |
| | | | 324/652 |
| 2009/0203315 A1* | 8/2009 | Kawabata | H03F 3/45179 |
| | | | 455/41.1 |
| 2013/0336095 A1* | 12/2013 | Seppa | G01L 9/0016 |
| | | | 367/137 |
| 2014/0138432 A1 | 5/2014 | Park et al. | |
| 2017/0110781 A1 | 4/2017 | Lee et al. | |
| 2018/0164281 A1* | 6/2018 | Beguin | B01L 3/502715 |
| 2018/0188201 A1 | 7/2018 | Park et al. | |
| 2018/0340903 A1* | 11/2018 | Heikenfeld | A61B 5/053 |

FOREIGN PATENT DOCUMENTS

| | | |
|---|---|---|
| KR | 10-2014-0063404 | 5/2014 |
| KR | 10-1575748 | 12/2015 |
| KR | 10-1680144 | 11/2016 |
| KR | 10-2017-0002112 A | 1/2017 |
| KR | 10-2017-0045963 | 4/2017 |
| KR | 10-2017-0045963 A | 4/2017 |

* cited by examiner

IC AND SENSOR FOR MEASURING SALINITY AND METHOD FOR MEASURING SALINITY USING THE SENSOR

CROSS-REFERENCE TO RELATED APPLICATION

This application claims priority under 35 U.S.C. § 119 from Korean Patent Application No. 10-2018-0118024 filed on Oct. 4, 2018 and 10-2018-0118018 filed on Oct. 4, 2018, the disclosures of which are hereby incorporated by reference in their entireties.

TECHNICAL FIELD

Embodiments of the present inventive concept relate to a salinity measuring device, and more particularly to an integrated circuit (IC) and a sensor which are capable of measuring salinity and a method for measuring salinity using the sensor.

DISCUSSION OF RELATED ART

Salt is used to season foods. Sodium of salt is brought into a human body through foods, and the salt is one of causes inducing hypertension that is an adult disease. Salt also affects myocardial infarction and stroke. Therefore, it is necessary to measure salinity included in a food and adjust the salinity of the food.

SUMMARY

An object of the present inventive concepts is to provide an IC without power supply, a sensor without power supply including the IC, and a method for salinity measurement using the sensor which can enable one of a plurality of driving signal generators and one of a plurality of analog-to-digital converters according to a characteristic or a type of a salinity sensor, and accurately measure salinity of a liquid to be sensed which is sensed by the salinity sensor using an enabled driving signal generator and an enabled analog-to-digital converter.

An exemplary embodiment of the present inventive concepts is directed to a sensor without power supply, including a first substrate which includes a top surface on which a sensing electrode and a ground electrode are disposed, and a bottom surface on which an IC chip connected to the sensing electrode and the ground electrode, and a first antenna electrode and a second antenna electrode connected to the IC chip are disposed, a second substrate which includes a first hole, a first layer which is disposed below the second substrate and in which a groove and an antenna having a structure of being connected to the first antenna electrode and the second antenna electrode are formed, and a transparent film which includes a second hole and is disposed on or above the second substrate, in which the bottom surface of the first substrate is inserted into the groove through the first hole and the second hole, and the IC chip includes a sensor driver circuit which transmits an analog driving signal to the sensing electrode through a pin of the IC chip, an analog-to-digital converter circuit which, if impedance between the sensing electrode and the ground electrode changes as a liquid to be sensed contacts with the sensing electrode and the ground electrode, receives an analog sensing signal generated according to a change of the impedance through the pin and converts it into a digital signal, and an RF interface which generates an operating voltage of the sensor driver circuit and an operating voltage of the analog-to-digital converter circuit on the basis of an RF signal received through the antenna.

Another exemplary embodiment of the present inventive concepts is directed to an integrated circuit (IC), including a bi-directional signal transmission pin which has a structure of being connected to a sensing electrode of a salinity sensor, an RF interface which generates operating voltages on the basis of an RF signal received through an antenna, different types of driving signal generators which have a structure in which each output terminal is connected to the bi-directional signal transmission pin, different types of analog-to-digital converters which have a structure in which each input terminal is connected to the bi-directional signal transmission pin, and a microcontroller unit which generates a first control signal and a second control signal according to a type of the salinity sensor, in which one of the different types of driving signal generators is enabled according to the first control signal, and one of the different types of analog-to-digital converters is enabled according to the second control signal, and the operating voltages are supplied to the enabled signal generator and the enabled analog-to-digital converter.

Still another exemplary embodiment of the present inventive concepts is directed to a method of measuring salinity of a liquid to be sensed using a mobile device and a sensor without power supply that transmits the salinity of the liquid to be sensed to the mobile device in response to a first RF signal transmitted from the mobile device, including transmitting, by an near-field communication (NFC) module, the first RF signal to the sensor without power supply under control of a mobile application program executed in the mobile device, generating, by an RF interface included in the sensor without power supply, operating voltages using the first RF signal received through an antenna included in the sensor without power supply, generating, by a microcontroller unit included in the sensor without power supply, a first control signal and a second control signal on the basis of a first operating voltage among the operating voltages, enabling one of different types of driving signal generators included in the sensor without power supply according to a second operating voltage among the operating voltages and the first control signal, and enabling one of different types of analog-to-digital converters included in the sensor without power supply according to a third operating voltage among the operating voltages and the second control signal, transmitting an analog driving signal generated by an enabled driving signal generator to a salinity sensor included in the sensor without power supply through a bi-directional signal transmission pin, converting, by an enabled analog-to-digital converter, an analog sensing signal received through the bi-directional signal transmission pin into a digital signal, transmitting, by the microcontroller unit, the salinity generated according to the digital signal to the NFC module as a second RF signal through the RF interface and the antenna, and analyzing, the mobile application program, a signal which is transmitted from the NFC module and corresponds to the second RF signal, and displaying a result of the analysis on a display device of the mobile device, in which the different types of driving signal generators are a square wave generator, a current generator, a voltage generator, and a signal generator, the different types of analog-to-digital converters are a voltage-to-digital converter and a time-to-digital converter, the enabled driving signal generator is one of the square wave generator, the current generator, and the voltage generator when the enabled analog-to-digital converter is the voltage-to-digital converter, the enabled driving signal generator is the signal generator when the enabled analog-to-digital converter is the time-to-digital converter, and the signal generator is a PWM signal generator or a sawtooth wave generator.

Still another exemplary embodiment of the present inventive concepts is directed to an NFC salinity-sensing module, including a first substrate which includes a top surface on which a sensing electrode and a ground electrode are disposed, and a bottom surface on which an IC chip connected to the sensing electrode and the ground electrode, and a first antenna electrode and a second antenna electrode connected to the IC chip are disposed, a second substrate which includes a first hole, a first layer which is disposed below the second substrate and in which a groove and an antenna having a structure of being connected to the first antenna electrode and the second antenna electrode are formed, and a transparent film which includes a second hole and is disposed on or above the second substrate, in which the bottom surface of the first substrate is inserted into the groove through the first hole and the second hole, and the IC chip includes a sensor driver circuit which transmits an analog driving signal to the sensing electrode through a pin of the IC chip, and an analog-to-digital converter circuit which, if impedance between the sensing electrode and the ground electrode changes as a liquid to be sensed contacts with the sensing electrode and the ground electrode, receives an analog sensing signal generated according to a change of the impedance through the pin and converts it into a digital signal, the ground electrode is electrically isolated from the sensing electrode, and the ground electrode completely surrounds the sensing electrode.

BRIEF DESCRIPTION OF THE DRAWINGS

These and/or other aspects and advantages of the present general inventive concept will become apparent and more readily appreciated from the following description of the embodiments, taken in conjunction with the accompanying drawings of which.

DETAILED DESCRIPTION OF EXEMPLARY EMBODIMENTS

Figure 1:
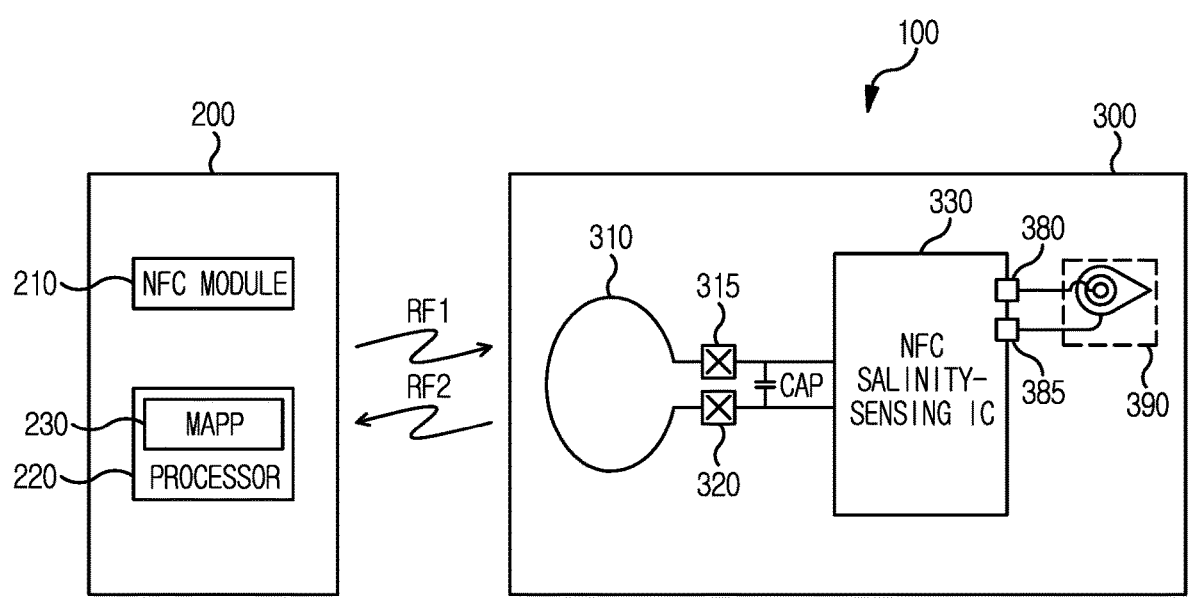
FIG. 1 is a block diagram of a salinity measurement system according to an exemplary embodiment of the present inventive concepts.

Reference will now be made in detail to the embodiments of the present general inventive concept, examples of which are illustrated in the accompanying drawings, wherein like reference numerals refer to the like elements throughout.

The embodiments are described below in order to explain the present general inventive concept by referring to the figures.

A device without power supply in the present specification (for example, an NFC salinity-sensing module 300 without power supply or an NFC salinity-sensing integrated circuit (IC) 330 without power supply) refers to a device which is capable of generating an operating voltage for the device without power supply using a radio frequency (RF) signal (for example, a near-field communication (NFC) signal) transmitted from an external power source (for example, a mobile device 200), without including a power source such as a battery therein, and transmitting or receiving signals to or from the external power source using the generated operating voltage.

FIG. 1 is a block diagram of a salinity measurement system according to an exemplary embodiment of the present inventive concepts. Referring to FIG. 1, a salinity measurement system 100 includes a mobile device 200 and a sensor without power supply (or the NFC salinity-sensing module without power supply) 300.

The mobile device 200 may be a device which is capable of supplying wireless power to the sensor without power supply 300, such as a smart phone, an internet of things (IoT) device, or an information & communication technology (ICT) device, and includes an NFC module 210 and a processor 220, and the processor 220 executes a mobile application program (simply, a mobile app 230). Under control of the mobile application program 230, the NFC module 210 transmits a first RF signal RF1 to the sensor without power supply 300 and transmits a signal corresponding to a second RF signal RF2 transmitted from the sensor without power supply 300 to the mobile application program 230.

The sensor without power supply 300 may refer to an ICT communication and sensing platform, and generates a voltage (or voltages) for an operation of the sensor without power supply 300 using the first RF signal RF1. The sensor without power supply 300 includes an antenna 310, antenna electrodes 315 and 320, a capacitor CAP, an NFC salinity-sensing IC without power supply (or an NFC salinity-sensing IC chip without power supply) 330, a plurality of pins 380 and 385, and a salinity sensor 390. The sensor without power supply 300 may perform a function of a passive NFC tag that does not include a battery therein.

Figure 2:
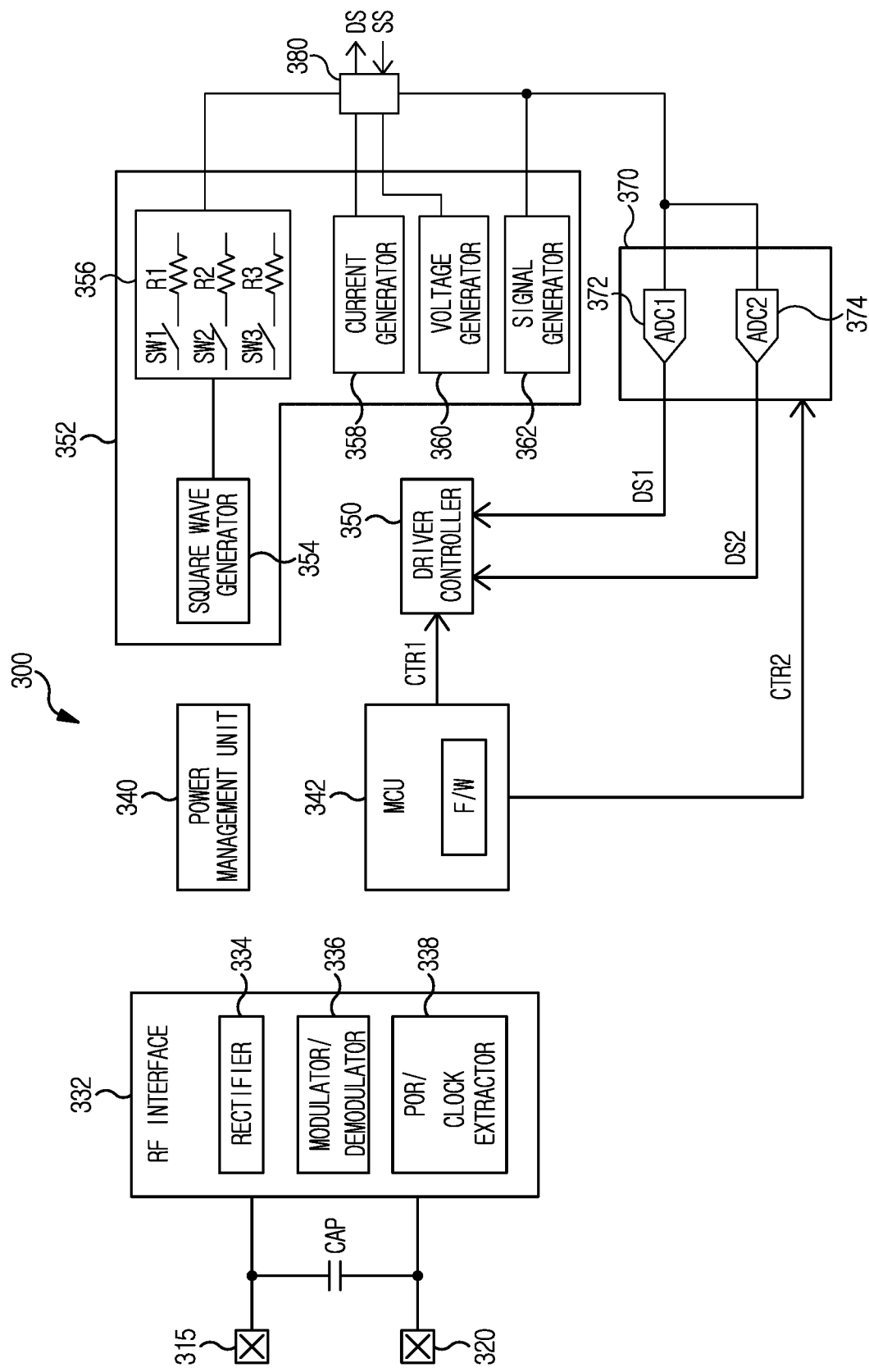
FIG. 2 is a block diagram of a near-field communication (NFC) salinity-sensing module without power supply shown in FIG. 1.

FIG. 2 is a block diagram of the NFC salinity-sensing module without power supply shown in FIG. 1. Referring to FIGS. 1 and 2, the antenna 310 may receive the first RF signal RF1 and transmit the second RF signal RF2.

The NFC salinity-sensing IC without power supply 330 includes an RF interface 332, a power management unit 340, a microcontroller unit (MCU) 342, a driver controller 350, a sensor driver circuit 352, an analog-to-digital converter circuit 370, and pins (pads or ports) 380 and 385. The MCU 342 may be a microcontroller.

The RF interface (or an RF interface circuit) 332 may generate a voltage for an operation of each of components 332, 340, 342, 350, 352, and/or 370 by using (for example, rectifying) the first RF signal RF1, generate data required for an operation of the NFC salinity-sensing IC without power supply 330 by demodulating the first RF signal RF1, and generate a second RF signal RF2 by modulating data to be transmitted to the mobile device 200.

The RF interface 332 may include a rectifier 334, a modulator/demodulator 336, and a power on reset (POR)/clock extractor 338.

The rectifier 334 generates operating voltages by rectifying the first RF signal RF1, and modulator/demodulator 336 generates (or extracts) first data included in the first RF signal RF1 by demodulating the first RF signal RF1, and generates a second RF signal RF2 corresponding to second data to be transmitted to the mobile device 200 by modulating the second data.

The POR/clock extractor 338 may perform a function of POR in response to a reception of the first signal RF1, and extract (or generate) a clock signal from a frequency of the first RF signal RF1. The clock signal (or a clock signal generated based on the clock signal) may be used as an operating clock of components (for example, the MCU 342, 358, 360, and/or 370) included in the NFC salinity-sensing IC without power supply 330.

The power management unit 340 may manage operating voltages generated by the rectifier 334, and control supply of the operating voltages to the components 332, 342, 350, 352, and/or 370.

The MCU 342 may execute firmware (F/W) included therein, and the firmware (F/W) may generate a first control signal CTR1 and a second control signal CTR2 according to a type (or a characteristic) of the salinity sensor 390. The firmware (F/W) may generate the first control signal CTR1 and the second control signal CTR2 or control a generation timing of each control signal CTR1 and CTR2 using data stored in an accessible non-volatile memory device, for example data representing a type or a characteristic of the salinity sensor 390.

The first control signal CTR1 collectively refers to control signals supplied to the driver controller 350 which is capable of controlling operations (for example, enabling and disabling) of components 354, 356, 358, 360, and 362 included in the sensor driver circuit 352.

The second control signal CTR2 collectively refers to control signals capable of controlling operations (for example, enabling and disabling) of components 372 and 374 included in the analog-to-digital converter circuit 370.

Enabling (or activating) means that a corresponding component is operated (for example, an operating voltage is supplied to the corresponding component), and disabling (or deactivating) means that a corresponding component is not operated (for example, an operating voltage is not supplied to the corresponding component).

The sensor driver circuit 352 includes a square wave generator 354 configured to generate a square wave, impedance matching resistors 356 formed between an output terminal of the square wave generator 354 and a pin (or a bi-directional signal transmission pin) 380, a current generator 358 connected to the pin 380, a voltage generator 360 connected to the pin 380, and a signal generator 362 connected to the pin 380.

According to the first control signal CTR1, the driver controller 350 performs an operation of enabling only one of the generators 354, 358, 360, and 362, and an operation of selecting one of the impedance matching resistors 356 when the square wave generator 354 is enabled. Each of the impedance matching resistors 356 includes respective switches SW1, SW2, and SW3 and respective resistors R1, R2, and R3, and resistance values of respective resistors R1, R2, and R3 are different from each other. Respective resistors R1, R2, and R3 may be selected by the driver controller 350 according to a sensing range of the salinity sensor 390.

When the square wave generator 354 is enabled, the driver controller 350 generates control signals to turn on one of the switches SW1, SW2, and SW3 on the basis of the first control signal CTR1. Each of the switches SW1, SW2, and SW3 may be embodied in a MOS FET; however, it is not limited thereto.

When the current generator 358 is enabled according to the first control signal CTR1, the current generator 358 supplies an analog current signal as a driving signal DS to the salinity sensor 390 through the pin 380. For example, the current generator 358 may be a digital-to-analog converter that outputs an analog current signal.

When the voltage generator 360 is enabled according to the first control signal CTR1, the voltage generator 360 supplies an analog voltage signal as a driving signal DS to the salinity sensor 390 through the pin 380. For example, the voltage generator 360 may be a digital-to-analog converter that outputs an analog voltage signal.

The signal generator 362 may be a signal generator configured to generate a pulse width modulation (PWM) signal or a signal generator configured to generate a sawtooth wave signal.

The analog-to-digital converter circuit 370 includes a voltage-to-digital converter (or a first analog-to-digital converter) 372 which converts a DC level corresponding to a sensing signal SS into a digital signal DS1, and a time-to-digital converter (or a second analog-to-digital converter) 374 which converts a PWM signal (or a sawtooth wave signal) corresponding to the sensing signal SS into a digital signal DS2. In an exemplary embodiment, the sensing signal SS may be an analog signal.

The voltage-to-digital converter collectively refers to a device which converts an input analog voltage (or current) into a digital number that represents a magnitude of the voltage (or the current), and the time-to-digital converter (TDC) collectively refers to a device which recognizes events and supplies digital expression of time at which the events occur, a device which outputs an arrival time of each reception pulse, or a device which measures a time interval and converts a measured time interval into a digital (or binary) output.

Assuming that the salinity sensor 390 receives a square wave as a driving signal DS, and shows or performs an optimal sensing function when a first impedance matching resistor including a first resistor R1 is selected, the MCU 342 generates a first control signal CTR1 that controls enabling of the square wave generator 354 and turning on of a first switch SW1 connected to the first resistor R1 among the impedance matching resistors 356, and outputs the first control signal CTR1 to the driver controller 350. Here, the firmware (F/W) of the MCU 342 generates control signals CTR1 and CTR2 by using (or referring to) data stored in an accessible non-volatile memory device.

Since the driver controller 350 enables the square wave generator 354 and turns on the first switch SW1 using the first control signal CTR1, square waves are supplied to the salinity sensor 390 through the first resistor R1 and the pin 380. That is, an output signal of a first impedance matching resistor is supplied to the salinity sensor 390 as a driving signal DS.

When the first control signal CTR1 is output to the driver controller 350, since the MCU 342 outputs a second control signal CTR2 which is used for enabling of the voltage-to-digital converter 372, the voltage-to-digital converter 372 receives the sensing signal SS received through the pin 380 and converts it into a digital signal DS1. For example, the components 354 and 372 may be enabled at the same time.

Assuming that the salinity sensor 390 shows or performs an optimal sensing function when the salinity sensor 390 receives an analog voltage signal (or an analog current signal) as a driving signal DS, the MCU 342 generates a first control signal CTR1 which controls enabling of the current generator 358 or the voltage generator 360 among the generators 354, 358, 360, and 362, and outputs the first control signal CTR1 to the driver controller 350. Here, the firmware (F/W) of the MCU 342 generates control signals CTR1 and CTR2 using (or referring to) data stored in an accessible non-volatile memory device.

The driver controller 350 enables the current generator 358 and the voltage generator 360 using the first control signal CTR1.

Since the MCU 342 outputs the second control signal CTR2 for enabling the voltage-to-digital converter 372 to the voltage-to-digital converter 372 when the first control signal CTR1 is output to the driver controller 350, the voltage-to-digital converter 372 receives the sensing signal SS received through the pin 380 and converts the sensing signal SS into a digital signal DS1. For example, the components (one of 358 and 360, and 372) may be enabled at the same time.

However, assuming that the salinity sensor 390 shows or performs the optimal sensing function when it receives a PWM signal or a sawtooth wave signal as a driving signal DS, the MCU 342 generates a first control signal CTR1 which controls enabling of a generator 362 for generating a PWM signal or a sawtooth wave signal among the generators 354, 358, 360, and 362, and outputs it to the driver controller 350. At this time, the firmware (F/W) of the MCU 342 generates the control signals (CTR1 and CTR2) by using (or referring to) the data stored in an accessible non-volatile memory device.

The driver controller 350 enables the generator 362 which generates a PWM signal or a sawtooth wave signal using the first control signal CTR1. For example, the components 362 and 374 may be enabled at the same time.

Since the MCU 342 outputs the second control signal CTR2 for enabling the time-to-digital converter 374 to the time-to-digital converter 374 when the first control signal CTR1 is output to the driver controller 350, the time-to-digital converter 374 receives the sensing signal SS received through the pin 380 and converts it into a digital signal DS2.

When an analog driving signal DS output from the enabled generator 354, 358, 360, or 362 is supplied to the salinity sensor 390, a waveform and/or level of the sensing signal SS is determined depending on whether a sensing electrode and a ground electrode included in the salinity sensor 390 are electrically connected to each other by a liquid to be sensed.

An impedance value of the salinity sensor 390 varies depending on whether the sensing electrode and the ground electrode are electrically connected to each other by a liquid to be sensed, and the waveform and/or level of the sensing signal SS reflect an impedance value (or a change in impedance value) of the salinity sensor 390, and reflects a concentration of impurity (for example, salinity) contained in the liquid to be sensed. For example, the waveform and/or level of the sensing signal SS vary with salinity contained in the liquid to be sensed.

Depending on how the first control signal CTR1 and the second control signal CTR2 are coded (or values of the first and second control signals CTR1 and CTR2) by firmware (F/W), only one of the generators 354, 358, 360, and 362 is enabled and only one of the analog-to-digital converters 372 and 374 is enabled.

Moreover, only one of the impedance matching resistors is selected depending on how the first control signal CTR1 is coded (or a value of the first control signal CTR1) by the firmware (F/W) when the square wave generator 354 is enabled.

A digital signal DS1 or DS2 output from the enabled analog-to-digital converter 372 or 374 is analyzed by the MCU 342, and a signal corresponding to a result of the analysis (for example, a signal corresponding to a salinity value) is modulated by the modulator/demodulator 336 and is transmitted to the NFC module 210 of the mobile device 200 as a second RF signal RF2.

Figure 3:
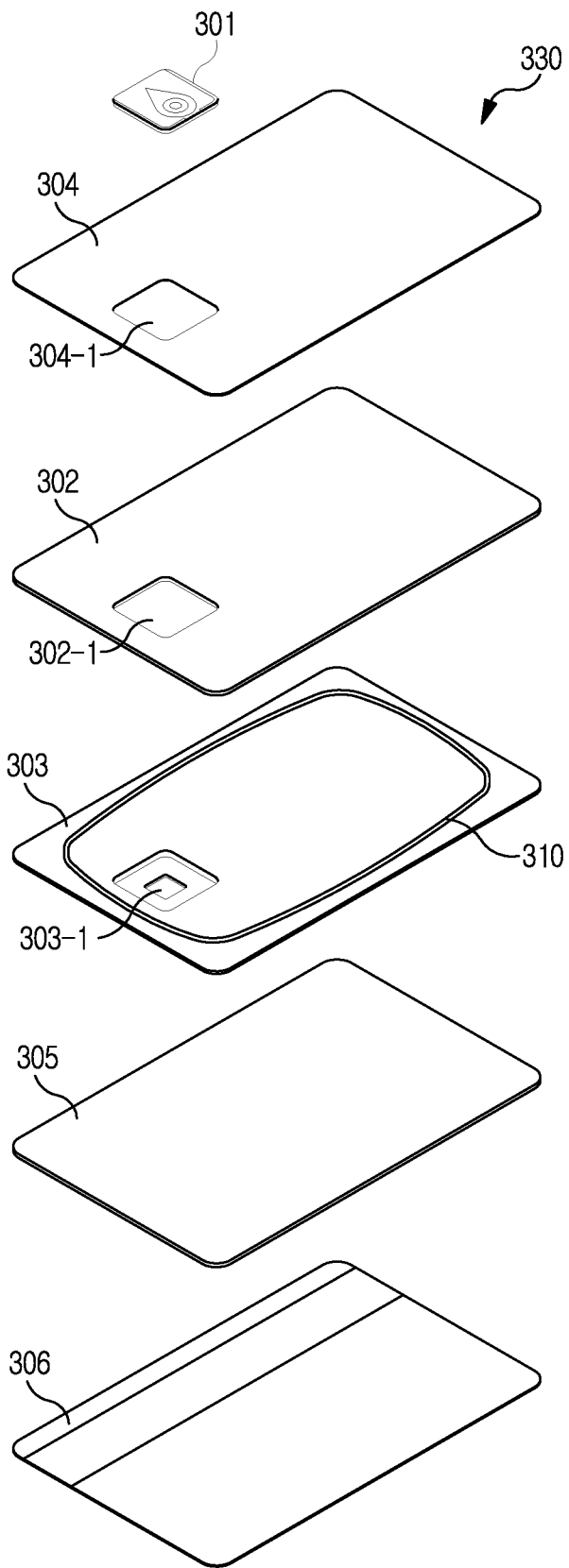
FIG. 3 shows a configuration diagram of the NFC salinity-sensing module without power supply shown in FIG. 1.
Figure 4A:
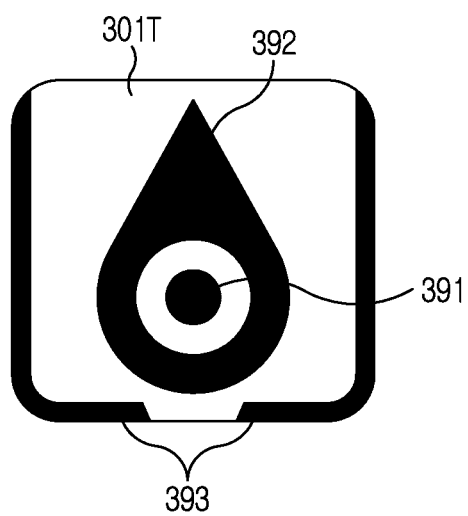
FIG. 4A shows electrodes disposed on a top surface of a first substrate shown in FIG. 3.
Figure 4B:
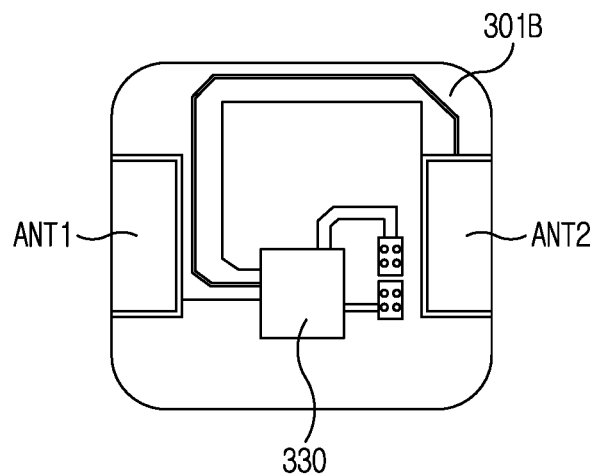
FIG. 4B shows an NFC salinity-sensing IC without power supply and antenna electrodes disposed on a bottom surface of the first substrate shown in FIG. 3.

FIG. 3 shows a configuration diagram of the NFC salinity-sensing module without power supply shown in FIG. 1, FIG. 4A shows electrodes disposed on a top surface of a first substrate shown in FIG. 3, and FIG. 4B shows an NFC salinity-sensing IC without power supply and antenna electrodes disposed on a bottom surface of the first substrate shown in FIG. 3.

Referring to FIGS. 1 to 4B, the sensor without power supply 300 in a credit card shape includes a first substrate 301, a second substrate 302, a first layer 303, a first transparent film 304, a second layer 305, and a second transparent film 306. As the sensor without power supply 300 is manufactured in a form of credit card, it is convenient to carry and to use.

A sensing electrode 391 and a ground electrode 392 of the salinity sensor 390 are formed (or disposed) on a top surface 301T of the first substrate 301, and the NFC salinity-sensing IC without power supply (or a semiconductor package) 330 electrically connected to the sensing electrode 391 and the ground electrode 392 through vias, and a first antenna electrode 315 or ANT1 and a second antenna electrode 320 or ANT2 electrically connected to the NFC salinity-sensing IC without power supply 330 are formed (or disposed) on a bottom surface 301B of the first substrate 301.

That is, since conductive electrodes 391 and 392 for performing a function of a salinity sensor and the NFC salinity-sensing IC without power supply 330 are disposed in the first substrate 301, the first substrate 301 may be referred to as a sensor module (for example, a salinity sensor module).

When the first substrate 301 is vertically cut, a bottom solder mask is formed at the bottom of the first substrate 301, a bottom layer is formed on or above the bottom solder mask, a core is formed on or above the bottom layer, a top layer is formed on or above the core, and a top solder mask is formed on or above the top layer.

The bottom layer is formed (or embodied) of copper for a connection with the NFC salinity-sensing IC without power supply 330 using a surface mount technology (SMT), the top layer is formed (or embodied) of copper to form (or connect) the sensing electrode 391 and the ground electrode 392, the core is formed of FR4 and has a thickness of 1.6 mm to 2.0 mm, and a thickness of the copper is embodied to be 18 μm (±2.5 μm) to 35 μm (±5 μm).

The sensing electrode 391 may be referred to as a sensor port, and is connected to a first pin 380, and the ground electrode 392 is connected to a second pin 385. The NFC salinity-sensing IC without power supply 330 may be attached to the bottom surface 301B in a form of flip chip or as a surface-mount device.

A first hole 302-1 in a rectangular shape is formed in the second substrate 302. The first layer 303 is disposed immediately below the second substrate 302, and an antenna (or an antenna pattern) 310 having a structure of being connected to the first antenna electrode ANT1 and the second antenna electrode ANT2 and a groove 303-1 are formed therein.

A second hole 304-1 in a rectangular shape is formed in the first transparent film 304. The second layer 305 is formed (or disposed) between the first layer 303 and the second transparent film 306.

Each of the transparent films 304 and 306 performs a function of overlay, the first layer 303 performs a function of inlay. Each of the second substrate 302 and the second layer 305 may be formed of polyvinyl chloride (PCV), polyethylene terephthalate (PET), or polyethylene terephthalate glycol (PETG). The bottom surface 301B of the first substrate 301 is inserted into the groove 303-1 through the holes 302-1 and 304-1.

Figure 5:
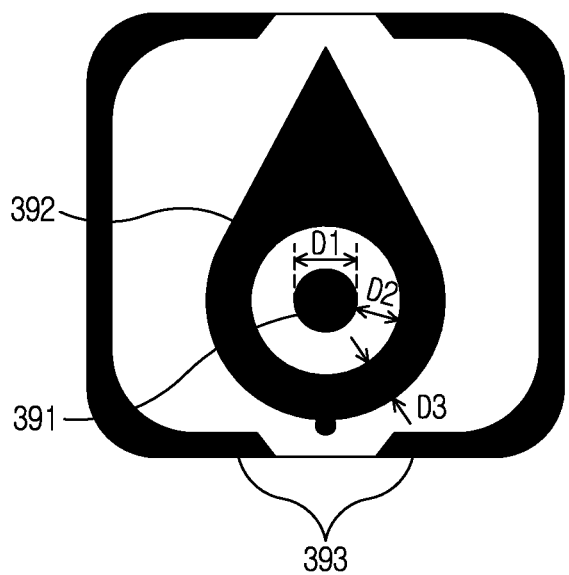
FIG. 5 shows a structure of the electrodes disposed on the top surface of the first substrate shown in FIG. 3.

FIG. 5 shows a structure of the electrodes disposed on the top surface of the first substrate shown in FIG. 3. Referring to FIG. 4A and FIG. 5, the sensing electrode 391, the ground electrode 392, and a liquid guide 393 are formed or disposed on the top surface 301T of the first substrate 301 in an exposed manner. The sensing electrode 391, the ground electrode 392, and the liquid guide 393 are formed on the same plane.

The ground electrode 392 is electrically isolated from the sensing electrode 391, the ground electrode 392 completely surrounds the sensing electrode 391, and the liquid guide 393 partially surrounds the ground electrode 392 and has a structure of preventing a liquid to be sensed from flowing down.

The sensing electrode 391 may be formed in a circular shape and the ground electrode 392 may be formed in a water droplet shape; however, shapes of the electrodes 391 and 392 according to an embodiment of the present invention are not limited thereto. A diameter D1 of the sensing electrode 391 is 1.7 mm±0.1 mm, a distance or gap D2 between the ground electrode 392 and the sensing electrode 391 is 1.2 mm±0.1 mm, and a width D3 of a circular portion of the ground electrode 392 is 1.2 mm±0.1 mm.

When a liquid to be sensed falls onto the sensing electrode 391 and is diffused according to configurations D1, D2, and D3 of the electrodes 391 and 392, the liquid to be sensed may short-circuit the electrodes 391 and 392.

For example, even if an amount of a liquid to be sensed is 1.0 ml (for example, a drop of liquid falling from a syringe (which may mean a minimum amount of liquid which can be sensed by the salinity sensor 390 when the sensor without power supply 300 including the salinity sensor 390 is routinely used according to exemplary embodiments), the liquid to be sensed can sufficiently fill the gap D2 according to the configurations D1, D2, and D3 of the electrodes 391 and 392, and thus the ground electrode 392 and the sensing electrode 391 may be short-circuited by the liquid to be sensed.

A ratio (S2/S1) of an area S2 of the ground electrode 392 to an area S1 of the sensing electrode 391 is embodied as 10 to 16. According to the ratio (S2/S1) of these areas S1 and S2, since a temperature of a liquid to be sensed that has fallen onto the salinity sensor 390 can be equal to an ambient temperature within a short period of time, the sensor without power supply 300 can measure or sense a salinity value of the liquid to be sensed within the short period of time.

Figure 6:
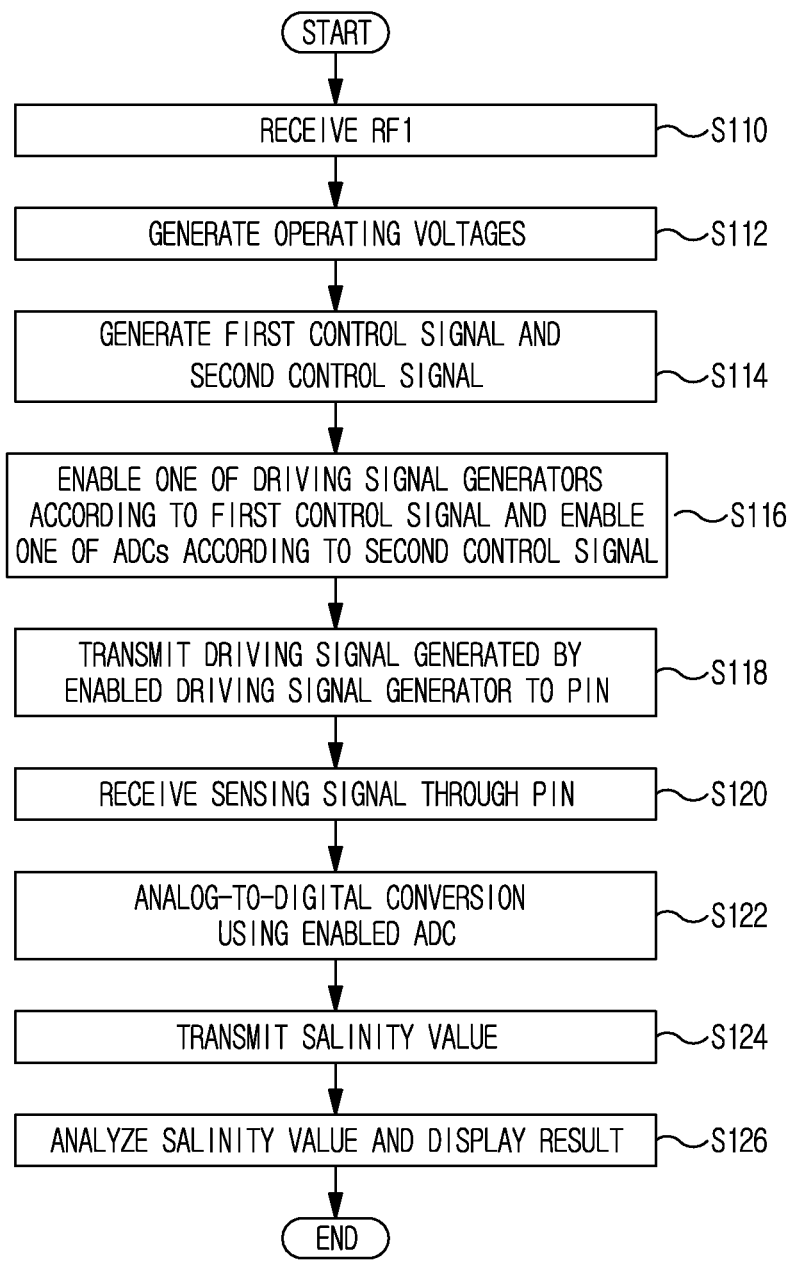
FIG. 6 is a flowchart which describes a method of operating the salinity measurement system shown in FIG. 1.

FIG. 6 is a flowchart which describes a method of operating the salinity measurement system shown in FIG. 1. Referring to FIGS. 1 to 6, a method of measuring salinity of a liquid to be sensed is performed by using the mobile device 200 and the sensor without power supply 300.

The sensor without power supply 300 transmits salinity (or a salinity value) of a liquid to be sensed to the mobile device 200 in response to a first RF signal RF1 transmitted from the mobile device 200.

When the NFC module 210 transmits the first RF signal RF1 to the sensor without power supply 300 under control of the mobile app 230 executed in the mobile device 200, the sensor without power supply 300 receives the first RF signal RF1 (S110). The first RF signal RF1 may be used as power of the sensor without power supply 300.

The rectifier 334 of the RF interface 332 generates operating voltages by rectifying the first RF signal RF1 received through the antenna 310 included in the sensor without power supply 300 (S112). The MCU 342 generates a first control signal CTR1 and a second control signal CTR2 by using a first operating voltage among the operating voltages under control of the firmware 344 (S114).

One of different types of driving signal generators 354, 358, 360, and 362 is enabled according to a second operating voltage among the operating voltages and the first control signal CTR1, and one of different types of analog-to-digital converters 372 and 374 is enabled according to a third operating voltage among the operating voltages and the second control signal CTR2 (S116). For example, a voltage level and a supply timing of each of the operating voltages may be controlled by the power management unit 340.

The analog driving signal DS generated by the driving signal generator 354, 358, 360, or 362 enabled on the basis of the first control signal CTR1 is transmitted to the salinity sensor 390 included in the sensor without power supply 300 through the bi-directional signal transmission pin 380 (S118).

When the analog driving signal DS is transmitted to the salinity sensor 390, the analog-to-digital converter 372 or 374 enabled on the basis of the second control signal CTR2 converts the sensing signal SS received through the bi-directional signal transmission pin 380 into a digital signal DS1 or DS2 (S120 and S122).

The MCU 342 transmits salinity or a salinity value generated on the basis of the digital signal DS1 or DS2 to the NFC module 210 as a second RF signal RF2 through the RF interface 332 and the antenna 310, and the NFC module 210 transmits a signal corresponding to the second RF signal RF2 to the mobile app 230 (S124).

The mobile app 230 analyzes the signal transmitted from the NFC module 210, and displays a result of the analysis on a display device of the mobile device 200 (S126).

The different types of driving signal generators are the square wave generator 354, the current generator 358, the voltage generator 360, and the signal generator 362, the different types of analog-to-digital converters are the voltage-to-digital converter 372 and the time-to-digital converter 374, and the driving signal generator enabled when the enabled analog-to-digital converter is the voltage-to-digital converter 372 is one of the square wave generator 354, the current generator 358, and the voltage generator 360.

The driving signal generator enabled when the enabled analog-to-digital converter is the time-to-digital converter 372 is the signal generator 362, and the signal generator 362 is a PWM signal generator or a sawtooth wave generator.

The first control signal CTR1 which enables only one of the square wave generator 354, the current generator 358, the voltage generator 360, and the signal generator 362, and the second control signal CTR2 which enables only one of the voltage-to-digital converter 372 and the time-to-digital converter 374 are determined according to a characteristic or a type of the salinity sensor 390.

Figure 7:
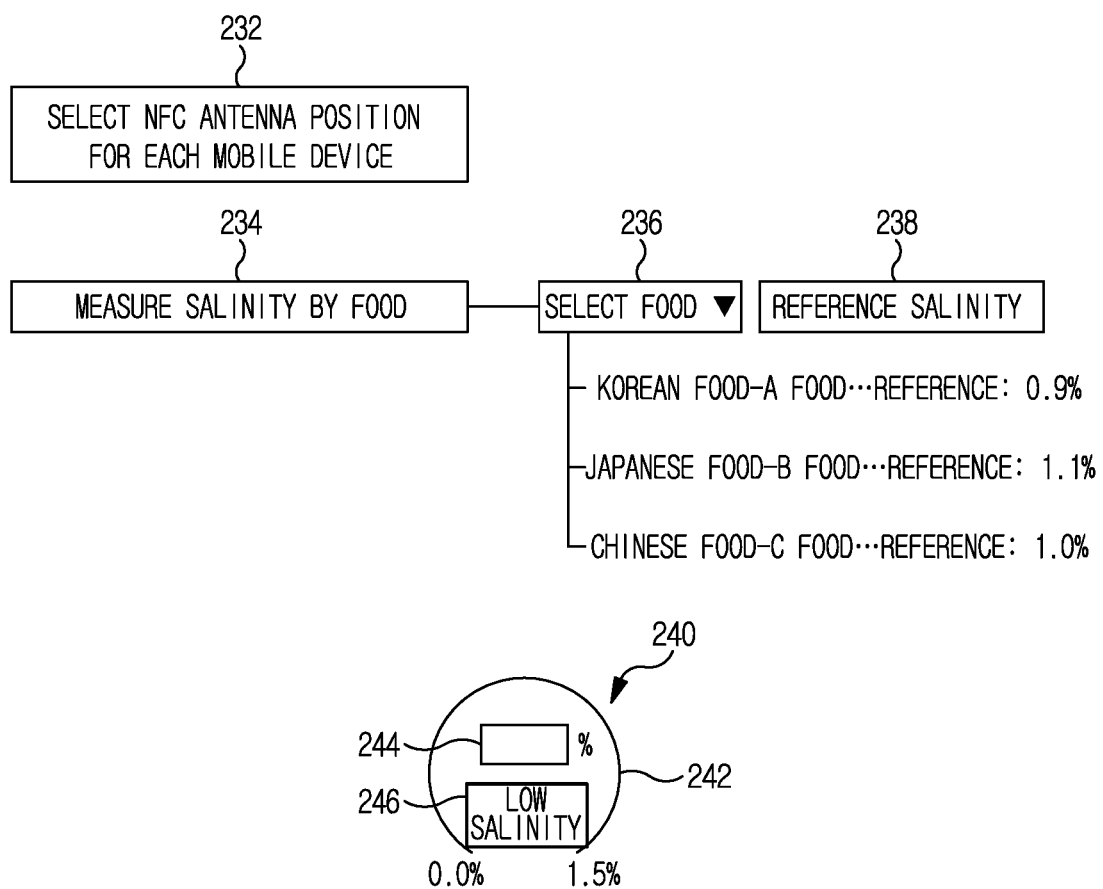
FIG. 7 is a conceptual diagram which describes a method of operating a mobile application program according to an exemplary embodiment of the present inventive concepts.

FIG. 7 is a conceptual diagram which describes a method of operating a mobile application program according to an exemplary embodiment of the present inventive concepts.

The method of operating the mobile application program 230 will be described with reference to FIG. 1 and FIG. 7.

Each of configurations 232, 234, 236, 238, 242, 244, and 246 may be embodied as a graphical user interface (GUI).

First, the mobile application program 230 may provide a user with a GUI 233 for selecting an NFC antenna position for each mobile device through the display device of the mobile device 200. Since the NFC antenna position for each mobile device may be different according to a model of a manufacturer of the mobile device 200, the user may select an NFC antenna suitable for the mobile device 200.

The mobile application program 230 may provide a user with a GUI 234 for salinity measurement by food through the display device of the mobile device 200. If the user touches a GUI 236 to select one of "Korean food," "Japanese food," and "Chinese food", and selects a corresponding food (for example, A food, B food, or C food), a reference value for the selected food (for example, 0.9%, 1.1%, or 1.0%) is displayed in a reference salinity GUI 238.

For example, when a user selects "Korean food," a list of food is displayed on the display device, and, when the user selects "A food" among the foods, reference salinity of the selected 'A food" (for example, a reference: 0.9%) is displayed in the GUI 238.

The mobile application program 230 may analyze the signal transmitted from the NFC module 210 (for example, a signal corresponding to the second RF signal RF2 and corresponding to salinity (or a salinity value) sensed by the salinity sensor 390), display a result of the analysis on a GUI 242 in a form of graph, and display salinity (or a salinity value) in a GUI 244 in a form of number. In addition, the mobile application program 230 may compare the salinity (or the salinity value) with the reference salinity, and display a result of the comparison in a GUI 246 using a character.

For example, the mobile application program 230 displays salinity of a liquid to be sensed as low salinity on the GUI 246 when salinity corresponding to the result of the analysis is lower than the reference salinity of the selected food, the mobile application program 230 displays the salinity of a liquid to be sensed as high salinity on the GUI 246 when the salinity is higher than the reference salinity, and the mobile application program 230 displays the salinity of a liquid to be sensed as appropriate salinity (or moderate salinity) on the GUI 246 when the salinity is within an error range of the reference salinity.

Therefore, the user can confirm how much the salinity of a selected food (or a liquid to be sensed) is higher or lower than the reference salinity of the selected food as well as numerically confirming the salinity of the selected good (or the liquid to be sensed) through the GUI 242 and/or 244.

The IC without power supply, the sensor without power supply including the IC without power supply, and the method of measuring salinity using the sensor according to an exemplary embodiment of the present inventive concepts can enable one of a plurality of driving signal generators and one of a plurality of analog-to-digital converters according to the characteristic or type of a salinity sensor, and accurately measure salinity of a liquid to be sensed which is sensed by the salinity sensor using the enabled driving signal generator and the enabled analog-to-digital converter.

Although the present general inventive concepts have been described with reference to exemplary embodiments shown in drawings, it will be appreciated by those skilled in the art that various changes and modifications may be made without departing from the scope of the present inventive concepts. Accordingly, the scope of the present inventive concepts needs to be determined by the technical concept defined in the appended claims and their equivalents.

What is claimed is:

1. A sensor without power supply comprising:
a first substrate which includes a top surface on which a sensing electrode and a ground electrode are disposed, and a bottom surface on which an IC chip connected to the sensing electrode and the ground electrode and a first antenna electrode and a second antenna electrode connected to the IC chip are disposed;
a second substrate which includes a first hole;
a first layer which is disposed below the second substrate and in which a groove and an antenna having a structure of being connected to the first antenna electrode and the second antenna electrode are formed; and
a transparent film which includes a second hole and is disposed on or above the second substrate,
wherein the bottom surface of the first substrate is inserted into the groove through the first hole and the second hole,
wherein the IC chip includes:
a sensor driver circuit transmitting an analog driving signal to the sensing electrode through a pin of the IC chip;
an analog-to-digital converter circuit receiving, if impedance between the sensing electrode and the ground electrode changes as a liquid to be sensed is contact with the sensing electrode and the ground electrode, an analog sensing signal generated according to a change of the impedance through the pin and converting the analog sensing signal into a digital signal; and
an RF interface generating an operating voltage of the sensor driver circuit and an operating voltage of the analog-to-digital converter circuit on the basis of an RF signal received through the antenna.

2. The sensor of claim 1, further comprising:
a driver controller,
wherein the sensor driver circuit includes:
a square wave generator generating a square wave;
impedance matching resistors formed between an output terminal of the square wave generator and the pin;
a current generator which is connected to the pin;
a voltage generator which is connected to the pin; and
a signal generator which is connected to the pin,
wherein the driver controller causes to enable one of the square wave generator, the current generator, the voltage generator, and the signal generator to generate the analog driving signal, and
wherein when the square wave generator is enabled and at least one of the impedance matching resistors is selected by the driver controller, the square wave corresponding to the analog driving signal generated by the square wave generator is supplied to the pin through the selected impedance matching resistor.

3. The sensor of claim 2,
wherein the analog-to-digital converter circuit includes a voltage-to-digital converter and a time-to-digital converter,
the voltage-to-digital converter is enabled when one of the square wave generator, the current generator, and the voltage generator is enabled,
the time-to-digital converter is enabled when the signal generator is enabled, and
the signal generator is a PWM signal generator or a sawtooth wave generator.

4. The sensor of claim 3, further comprising:
a microcontroller unit controlling an operation of the driver controller, an operation of the voltage-to-digital converter, and an operation of the time-to-digital converter according to a type of a salinity sensor including the sensing electrode and the ground electrode.

5. The sensor of claim 4, further comprising:
a liquid guide which is disposed on the top surface and prevents the liquid to be sensed from flowing down,
wherein the ground electrode is electrically isolated from the sensing electrode,
wherein the ground electrode completely surrounds the sensing electrode, and
wherein the liquid guide partially surrounds the ground electrode.

6. A salinity measurement system comprising:
a bi-directional signal transmission pin which has a structure of being connected to a sensing electrode of a salinity sensor;
an RF interface configured to generate operating voltages on the basis of an RF signal received through an antenna;
different types of driving signal generators which have a structure in which each output terminal is connected to the bi-directional signal transmission pin;
different types of analog-to-digital converters which have a structure in which each input terminal is connected to the bi-directional signal transmission pin; and
a microcontroller unit configured to generate a first control signal and a second control signal according to a type of the salinity sensor,
wherein one of the different types of driving signal generators is enabled according to the first control signal, and one of the different types of analog-to-digital converters is enabled according to the second control signal, and
the operating voltages are supplied to the enabled driving signal generator and the enabled analog-to-digital converter.

7. The salinity measurement system of claim 6,
wherein the different types of driving signal generators are a square wave generator, a current generator, a voltage generator, and a signal generator,
the different types of analog-to-digital converters are a voltage-to-digital converter and a time-to-digital converter,
the enabled driving signal generator is one of the square wave generator, the current generator, and the voltage generator when the enabled analog-to-digital converter is the voltage-to-digital converter,
the enabled driving signal generator is the signal generator when the enabled analog-to-digital converter is the time-to-digital converter, and
the signal generator is a PWM signal generator or a sawtooth wave signal generator.

8. A method of measuring salinity of a liquid to be sensed using a mobile device and a sensor without power supply that transmits the salinity of the liquid to be sensed to the mobile device in response to a first RF signal transmitted from the mobile device, the method comprising:
transmitting, by an NFC module under control of a mobile application program executed in the mobile device, the first RF signal to the sensor without power supply;
generating, by an RF interface included in the sensor without power supply, operating voltages using the first RF signal received through an antenna included in the sensor without power supply;
generating, by a microcontroller unit included in the sensor without power supply, a first control signal and a second control signal on the basis of a first operating voltage among the operating voltages;
enabling one of different types of driving signal generators included in the sensor without power supply according to a second operating voltage among the operating voltages and the first control signal, and enabling one of different types of analog-to-digital converters included in the sensor without power supply according to a third operating voltage among the operating voltages and the second control signal;
transmitting an analog driving signal generated by the enabled driving signal generator to a salinity sensor included in the sensor without power supply through a bi-directional signal transmission pin;
converting, by the enabled analog-to-digital converter, an analog sensing signal received through the bi-directional signal transmission pin to a digital signal;
transmitting, by the microcontroller unit, the salinity generated according to the digital signal to the NFC module as a second RF signal through the RF interface and the antenna; and
analyzing, the mobile application program, a signal which is transmitted from the NFC module and corresponds to the second RF signal, and displaying a result of the analysis on a display device of the mobile device,
wherein the different types of driving signal generators are a square wave generator, a current generator, a voltage generator, and a signal generator,
the different types of analog-to-digital converters are a voltage-to-digital converter and a time-to-digital converter,
the enabled driving signal generator is one of the square wave generator, the current generator, and the voltage generator when the enabled analog-to-digital converter is the voltage-to-digital converter,
the enabled driving signal generator is the signal generator when the enabled analog-to-digital converter is the time-to-digital converter, and
the signal generator is a PWM signal generator or a sawtooth wave generator.

9. The method of claim 8,
wherein the first control signal that enables one of the square wave generator, the current generator, the voltage generator, and the signal generator, and the second control signal that enables one of the voltage-to-digital converter and the time-to-digital converter are determined according to a type of the salinity sensor.

10. An NFC salinity-sensing module comprising:
a first substrate which includes a top surface on which a sensing electrode and a ground electrode are disposed, and a bottom surface on which an IC chip connected to the sensing electrode and the ground electrode and a first antenna electrode and a second antenna electrode connected to the IC chip are disposed;
a second substrate which includes a first hole;
a first layer which is disposed below the second substrate and in which a groove and an antenna having a structure of being connected to the first antenna electrode and the second antenna electrode are formed; and
a transparent film which includes a second hole and is disposed on or above the second substrate,
wherein the bottom surface of the first substrate is inserted into the groove through the first hole and the second hole, wherein the IC chip includes:
a sensor driver circuit which transmits an analog driving signal to the sensing electrode through a pin of the IC chip; and
an analog-to-digital converter circuit which, when impedance between the sensing electrode and the ground electrode changes as a liquid to be sensed contacts with the sensing electrode and the ground electrode, receives an analog sensing signal generated according to a change of the impedance through the pin and converts the analog sensing signal into a digital signal,
wherein the ground electrode is electrically isolated from the sensing electrode, and the ground electrode completely surrounds the sensing electrode.

11. The NFC salinity-sensing module of claim 10, wherein a diameter of the sensing electrode is 1.7 mm±0.1 mm,
a gap between the ground electrode and the sensing electrode is 1.2 mm±0.1 mm, and a width of a circular portion of the ground electrode is 1.2 mm±0.1 mm.

12. The NFC salinity-sensing module of claim 11, wherein a ratio (S2/S1) of an area (S2) of the ground electrode to an area (S1) of the sensing electrode is 10 to 16.

13. The NFC salinity-sensing module of claim 11, further comprising:
a driver controller,
wherein the sensor driver circuit includes:
a square wave generator which generates a square wave;
impedance matching resistors which are formed between an output terminal of the square wave generator and the pin;
a current generator which is connected to the pin;
a voltage generator which is connected to the pin; and
a signal generator which is connected to the pin,
wherein the driver controller enables only one of the square wave generator, the current generator, the voltage generator, and the signal generator to generate the analog driving signal, and when the square wave generator is enabled and one of the impedance matching resistors is selected by the driver controller, the square wave corresponding to the analog driving signal generated by the square wave generator is supplied to the pin through the selected impedance matching resistor.

14. The NFC salinity-sensing module of claim 13, wherein the analog-to-digital converter circuit includes:
a voltage-to-digital converter; and
a time-to-digital converter,
wherein the voltage-to-digital converter is enabled when one of the square wave generator, the current generator, and the voltage generator is enabled,
the time-to-digital converter is enabled when the signal generator is enabled, and
the signal generator is a PWM signal generator or a sawtooth wave generator.

15. The NFC salinity-sensing module of claim 10, further comprising:
a liquid guide which is disposed on the top surface and prevents the liquid to be sensed from flowing down,
wherein the ground electrode is electrically isolated from the sensing electrode, the ground electrode completely surrounds the sensing electrode, and the liquid guide partially surrounds the ground electrode.

16. The NFC salinity-sensing module of claim 15, wherein a diameter of the sensing electrode is 1.7 mm±0.1 mm,
a gap between the ground electrode and the sensing electrode is 1.2 mm±0.1 mm,
a width of a circular portion of the ground electrode is 1.2 mm±0.1 mm, and
a ratio of an area of the ground electrode to an area of the sensing electrode is 10 to 16.

* * * * *